(12) United States Patent
Gabbay

(10) Patent No.: US 7,169,402 B2
(45) Date of Patent: Jan. 30, 2007

(54) ANTIMICROBIAL AND ANTIVIRAL POLYMERIC MATERIALS

(75) Inventor: Jeffrey Gabbay, Jerusalem (IL)

(73) Assignee: The Cupron Corporation, New York, NY (US)

(*) Notice: Subject to any disclaimer, the term of this patent is extended or adjusted under 35 U.S.C. 154(b) by 38 days.

(21) Appl. No.: 10/240,993

(22) PCT Filed: Apr. 1, 2001

(86) PCT No.: PCT/IL01/00299

§ 371 (c)(1),
(2), (4) Date: Dec. 16, 2002

(87) PCT Pub. No.: WO01/74166

PCT Pub. Date: Oct. 11, 2001

(65) Prior Publication Data

US 2004/0224005 A1 Nov. 11, 2004

(30) Foreign Application Priority Data

Apr. 5, 2000 (IL) .................................. 135 487

(51) Int. Cl.
*A01N 25/34* (2006.01)
(52) U.S. Cl. .............. 424/404; 424/405; 424/409; 424/411; 424/421; 424/635; 424/78.07; 523/122; 524/440; 514/841; 514/842; 514/843; 2/161.7; 2/901; 128/844
(58) Field of Classification Search .......... 424/404, 424/405, 409, 411, 421, 630–637; 524/440; 523/122
See application file for complete search history.

(56) References Cited

U.S. PATENT DOCUMENTS

| 252,524 A | 1/1882 | Sagendorf |
| 1,210,375 A | 12/1916 | Decker |
| 1,947,451 A | 2/1934 | Barber et al. |
| 3,014,818 A * | 12/1961 | Campbell .................... 428/549 |
| 3,308,488 A | 3/1967 | Schoonman |
| 3,385,915 A | 5/1968 | Hamling |
| 3,663,182 A | 5/1972 | Hamling |
| 3,769,060 A | 10/1973 | Ida et al. |
| 3,821,163 A * | 6/1974 | Spivak ....................... 524/239 |
| 3,860,529 A | 1/1975 | Hamling |
| 4,072,784 A | 2/1978 | Cirinet |
| 4,103,450 A | 8/1978 | Whitcomb |

(Continued)

FOREIGN PATENT DOCUMENTS

DE 4403016 A1 8/1995

(Continued)

OTHER PUBLICATIONS

"Encyclopedia of Polymer Science and Technology," John Wiley & Sons, Inc., (1968) vol. 8, pp. 651-666 and vol. 9, pp. 580-598.

(Continued)

*Primary Examiner*—Neil S. Levy
(74) *Attorney, Agent, or Firm*—Townsend and Townsend and Crew LLP

(57) ABSTRACT

The invention provides an antimicrobial and antiviral polymeric material, having microscopic particles of ionic copper encapsulated therein and protruding from surfaces thereof.

34 Claims, 2 Drawing Sheets

U.S. PATENT DOCUMENTS

Figure 1:
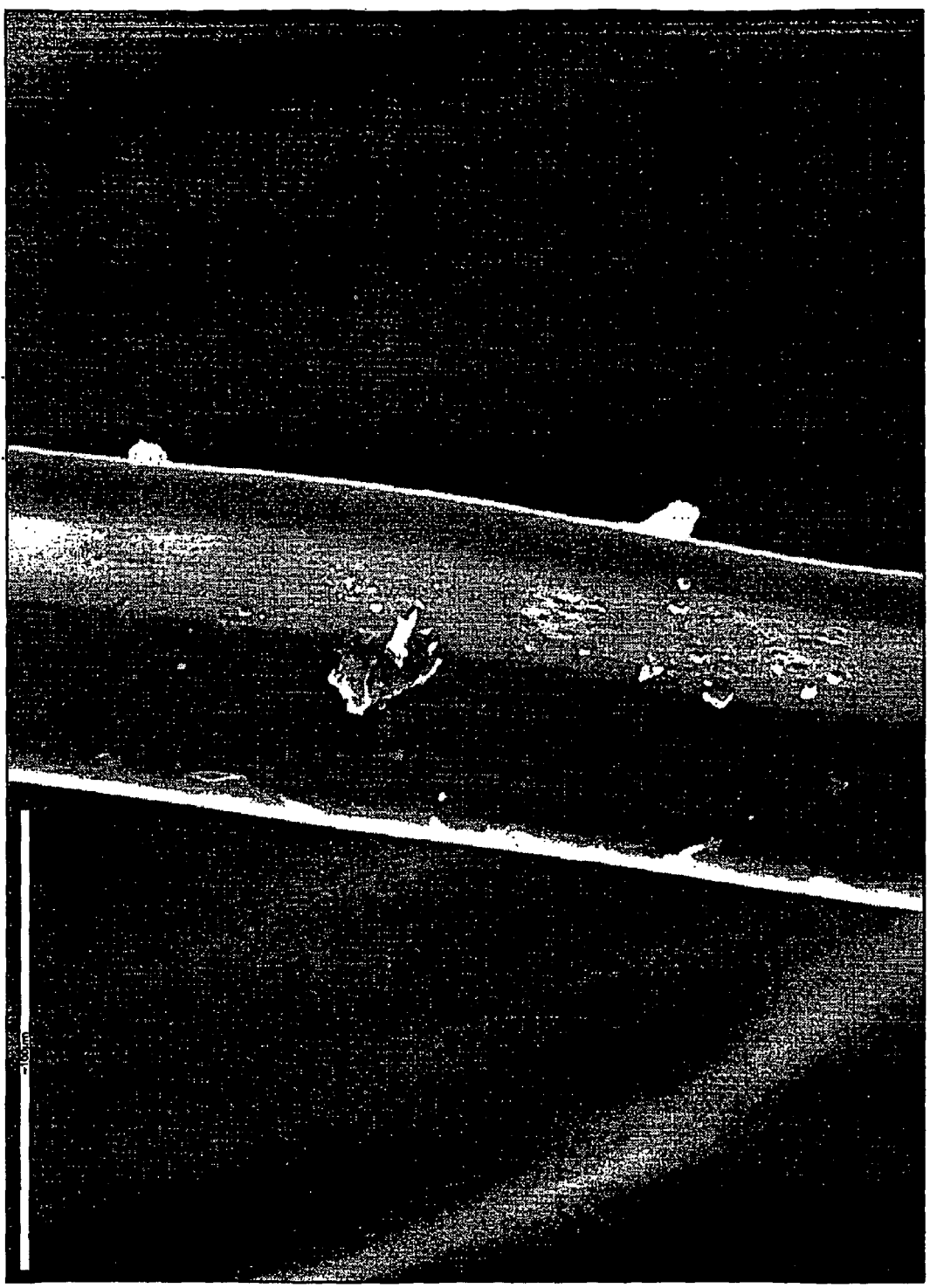

| | | |
|---|---|---|
| 4,115,422 A | 9/1978 | Welch et al. |
| 4,174,418 A | 11/1979 | Welch et al. |
| 4,201,825 A | 5/1980 | Ebneth |
| 4,219,602 A | 8/1980 | Conklin |
| 4,278,435 A | 7/1981 | Ebneth |
| 4,291,086 A | 9/1981 | Auten |
| 4,292,882 A | 10/1981 | Clausen |
| 4,317,856 A | 3/1982 | Huthelker et al. |
| 4,366,202 A | 12/1982 | Borovsky |
| 4,390,585 A | 6/1983 | Holden |
| 4,525,410 A | 6/1985 | Hagiwara |
| 4,666,940 A | 5/1987 | Bischoff et al. |
| 4,675,014 A | 6/1987 | Sustmann et al. |
| 4,710,184 A | 12/1987 | Ehret |
| 4,769,275 A | 9/1988 | Inagaki et al. |
| 4,835,019 A | 5/1989 | White et al. |
| 4,900,618 A | 2/1990 | O'Connor et al. |
| 4,900,765 A | 2/1990 | Murabayashi et al. |
| 4,983,573 A | 1/1991 | Bolt et al. |
| 4,999,240 A | 3/1991 | Brotz |
| 5,009,946 A | 4/1991 | Hatomoto et al. |
| 5,017,420 A | 5/1991 | Marikar et al. |
| 5,024,875 A | 6/1991 | Hill et al. |
| 5,066,538 A | 11/1991 | Huykman |
| 5,143,769 A | 9/1992 | Moriya et al. |
| 5,175,040 A | 12/1992 | Harpell et al. |
| 5,180,585 A | 1/1993 | Jacobson |
| 5,200,256 A | 4/1993 | Dunbar |
| 5,217,626 A | 6/1993 | Yahya et al. |
| 5,227,365 A | 7/1993 | Van Den Sype |
| 5,254,134 A | 10/1993 | Zhao et al. |
| 5,269,973 A | 12/1993 | Takahashi et al. |
| 5,316,837 A | 5/1994 | Cohen |
| 5,316,846 A | 5/1994 | Pinsky et al. |
| 5,370,934 A | 12/1994 | Burch et al. |
| 5,399,425 A | 3/1995 | Burch |
| 5,405,644 A | 4/1995 | Ohsumi et al. |
| 5,407,743 A | 4/1995 | Clough et al. |
| 5,411,795 A | 5/1995 | Silverman |
| 5,458,906 A | 10/1995 | Liang |
| 5,492,882 A | 2/1996 | Doughty et al. |
| 5,518,812 A | 5/1996 | Mitchnick et al. |
| 5,547,610 A | 8/1996 | Mortenson |
| 5,549,972 A | 8/1996 | Hsu et al. |
| 5,744,222 A | 4/1998 | Sugihara |
| 5,848,592 A | 12/1998 | Sibley |
| 5,849,235 A | 12/1998 | Sassa et al. |
| 5,856,248 A | 1/1999 | Weinberg |
| 5,869,412 A | 2/1999 | Yenni, Jr. et al. |
| 5,871,816 A | 2/1999 | Tal |
| 5,881,353 A | 3/1999 | Kamigata et al. |
| 5,904,854 A | 5/1999 | Shmidt et al. |
| 5,939,340 A | 8/1999 | Gabbay |
| 5,981,066 A | 11/1999 | Gabbay |
| 6,013,275 A | 1/2000 | Konagaya et al. |
| 6,124,221 A | 9/2000 | Gabbay |
| 6,383,273 B1 | 5/2002 | Kepner et al. |
| 6,394,281 B2 | 5/2002 | Ritland et al. |
| 6,482,424 B1 | 11/2002 | Gabbay |
| 2003/0198945 A1 | 10/2003 | Gabbay |
| 2003/0199018 A1 | 10/2003 | Gabbay |
| 2004/0167483 A1 | 8/2004 | Gabbay |
| 2004/0167484 A1 | 8/2004 | Gabbay |
| 2004/0167485 A1 | 8/2004 | Gabbay |
| 2004/0197386 A1 | 10/2004 | Gabbay |
| 2005/0048131 A1 | 3/2005 | Gabbay |
| 2005/0049370 A1 | 3/2005 | Gabbay |

FOREIGN PATENT DOCUMENTS

| | | |
|---|---|---|
| EP | 116 825 | 8/1984 |
| EP | 253 653 | 1/1989 |
| EP | 427 858 | 5/1991 |
| FR | 1499358 A | 9/1967 |
| FR | 2764518 | 6/1997 |
| GB | 415213 | 8/1934 |
| GB | 1382820 | 12/1971 |
| JP | 01-246204 | 3/1988 |
| JP | 63-088007 | 4/1988 |
| JP | 01-046465 | 2/1989 |
| JP | 01-046485 | 2/1989 |
| JP | 01-246204 | 10/1989 |
| JP | 02-161954 | 6/1990 |
| JP | 03-113011 | 5/1991 |
| JP | 8-113874 A | 5/1996 |
| WO | WO 94/15463 | 7/1994 |
| WO | WO 98/06508 A1 | 2/1998 |
| WO | WO 98/06509 A1 | 2/1998 |
| WO | WO 00/75415 A1 | 12/2000 |
| WO | WO 01/28337 A2 | 4/2001 |
| WO | WO 01/74166 | 10/2001 |
| WO | WO 01/81671 | 11/2001 |

OTHER PUBLICATIONS

Marino, A. et al., "Electrochemical Properties of Silver-Nylon Fabrics," J. Electrochem. Soc. (1985) vol. 132, No. 1, pp. 68-72.

Gabbay et al., "Copper Oxide Impregnated Textiles with Potent Biocidal Activities" Journal of Industrial Textiles, vol. 35, No. 4, 323-35, Apr. 2006.

* cited by examiner

ANTIMICROBIAL AND ANTIVIRAL POLYMERIC MATERIALS

CROSS-REFERENCE TO RELATED APPLICATIONS

This application is a National Phase of PCT/IL01/00299 (filed 1 Apr. 2001) which claims priority to Israel patent application No. 135487 (filed 5 Apr. 2000).

The present invention relates to an antimicrobial and antiviral polymeric material and to a process for preparing the same. More particularly, the present invention relates to an antimicrobial polymeric material useful as a wrapping material for agricultural produce, as well as to an antiviral polymeric material useful for the formation of a condom sheath, surgical tubing and surgical gloves.

A problem faced by all food exporters is the attack on the agricultural produce after it has been harvested by microorganisms while in transport. This is especially true when the transportation is measured in days, weeks, or months, rather than hours. Microorganisms are known to cause severe damage to the produce, resulting in added costs which are passed on to the consumer. An example of this is the strawberry harvest in Israel. Every year about 50% of the harvest is lost while in transportation due to the attack of microorganisms. To date, there has been no effective system developed that can effectively reduce the waste rate.

There are many wrapping materials used in food transport from burlap bags to sophisticated polymer wrappings that demonstrate qualities such as strength, flexibility, breathability and are inexpensive. However, none to date are able to control the growth of microorganisms that flourish in packaged, agricultural produce.

According to the present invention it has now been discovered that by adding a small percentage of Cu++ in powder form to the slurry of a polymer to be formed into a wrapping material, the package is rendered antimicrobial.

It has also been surprisingly discovered that by adding Cu++ in powder form to the slurry of a polymer to be formed into a condom there is produced a condom which inhibits and reduces active HIV-1 in body fluids.

Similarly, surgical gloves and surgical tubing having antimicrobial and antiviral properties can be prepared according to the present invention.

In both WO 98/06508 and WO 98/06509 there are taught various aspects of a textile with a full or partial metal or metal oxide plating directly and securely bonded to the fibers thereof, wherein metal and metal oxides, including copper, are bonded to said fibers.

More specifically, in WO 98/06509 there is provided a process comprising the steps of: (a) providing a metallized textile, the metallized textile comprising: (i) a textile including fibers selected from the group consisting of natural fibers, synthetic cellulosic fibers, regenerated fibers, acrylic fibers, polyolefin fibers, polyurethane fibers, vinyl fibers, and blends thereof, and (ii) a plating including materials selected from the group consisting of metals and metal oxides, the metallized textile characterized in that the plating is bonded directly to the fibers; and (b) incorporating the metallized textile in an article of manufacture.

In the context of said invention the term "textile" includes fibers, whether natural (for example, cotton, silk, wool, and linen) or synthetic yarns spun from those fibers, and woven, knit, and non-woven fabrics made of those yarns. The scope of said invention includes all natural fibers; and all synthetic fibers used in textile applications, including but not limited to synthetic cellulosic fibers (i.e., regenerated cellulose fibers such as rayon, and cellulose derivative fibers such as acetate fibers), regenerated protein fibers, acrylic fibers, polyolefin fibers, polyurethane fibers, and vinyl fibers, but excluding nylon and polyester fibers, and blends thereof.

Said invention comprised application to the products of an adaptation of technology used in the electrolyses plating of plastics, particularly printed circuit boards made of plastic, with metals. See, for example, Encyclopedia of Polymer Science and Engineering (Jacqueline I. Kroschwitz, editor), Wiley and Sons, 1987, vol. IX, pp 580–598. As applied to textiles, this process included two steps. The first step was the activation of the textile by precipitating catalytic noble metal nucleation sites on the textile. This was done by first soaking the textile in a solution of a low-oxidation-state reductant cation, and then soaking the textile in a solution of noble metal cations, preferably a solution of Pd++ cations, most preferably an acidic $PdCl_2$ solution. The low-oxidation-state cation reduces the noble metal cations to the noble metals themselves, while being oxidized to a higher oxidation state. Preferably, the reductant cation is one that is soluble in both the initial low oxidation state and the final high oxidation state, for example Sn++, which is oxidized to Sn++++, or Ti+++, which is oxidized to Ti++++.

The second step was the reduction, in close proximity to the activated textile, of a metal cation whose reduction was catalyzed by a noble metal. The reducing agents used to reduce the cations typically were molecular species, for example, formaldehyde in the case of Cu++. Because the reducing agents were oxidized, the metal cations are termed "oxidant cations" herein. The metallized textiles thus produced were characterized in that their metal plating was bonded directly to the textile fibers.

In WO 98/06508 there is described and claimed a composition of matter comprising:

(a) a textile including fibers selected from the group consisting of natural fibers, synthetic cellulosic fibers, regenerated protein fibers, acrylic fibers, polyolefin fibers, polyurethane fibers, vinyl fibers, and blends thereof; and (b) a plating including materials selected from the group consisting of metals and metal oxides; the composition of matter characterized in that said plating is bonded directly to said fibers.

Said publication also claims a composition of matter comprising:

(a) a textile including fibers selected from the group consisting of natural fibers, synthetic cellulosic fibers, regenerated protein fibers, acrylic fibers, polyolefin fibers, polyurethane fibers, vinyl fibers, and blends thereof; and (b) a plurality of nucleation sites, each of said nucleation sites including at least one noble metal; the composition of matter characterized by catalyzing the reduction of at least one metallic cationic species to a reduced metal, thereby plating said fibers with said reduced metal.

In addition, said publication teaches and claims processes for producing said products.

A preferred process for preparing a metallized textile according to said publication comprises the steps of:

a) selecting a textile, in a form selected from the group consisting of yarn and fabric, said textile including fibers selected from the group consisting of natural fibers, synthetic cellulosic fibers, regenerated protein fibers, acrylic fibers, polyolefin fibers, polyurethane fibers, vinyl fibers, and blends thereof;

b) soaking said textile in a solution containing at least one reductant cationic species having at least two positive oxidation states, said at least one cationic species being in a lower of said at least two positive oxidation states;

c) soaking said textile in a solution containing at least one noble metal cationic species, thereby producing an activated textile; and d) reducing at least one oxidant cationic species in a medium in contact with said activated textile, thereby producing a metallized textile.

Said publications, however, are limited to coated fibers and textiles prepared according to said processes and do not teach or suggest the possibility of incorporating ionic copper into a polymeric slurry whereby there are produced films and fibers having microscopic particles of ionic copper encapsulated therein and protruding therefrom and having antimicrobial and antiviral polymeric properties, as described and exemplified herein.

With this state of the art in mind there is now provided according to the present invention an antimicrobial and antiviral polymeric material, having microscopic water insoluble particles of ionic copper in powder form, which release $C^{++}$ encapsulated therein with a portion of said particles being exposed and protruding from surfaces thereof.

In another aspect of the present invention there is provided a process for preparing an antimicrobial and antiviral polymeric material, comprising preparing a polymeric slurry, introducing an ionic copper powder and dispersing the same in said slurry and then extruding said slurry to form a polymeric material wherein water insoluble particles that release $C^{++}$ are encapsulated therein with a portion of said particles being exposed and protruding from surfaces thereof.

The polymeric material of the present invention can be in the form of a film, a fiber, or a yam, wherein said films are used per se and said fibers and yams can be formed into a packaging material for agricultural products.

Said material can be made from almost any synthetic polymer, which will allow the introduction of an anionic, copper dust into its liquid slurry state. Examples of some materials are polyamides (nylon), polyester, acrylic, polypropylene, silastic rubber and latex When the copper dust is ground down to fine powder, e.g., a size of between 1 and 10 microns and introduced into the slurry in small quantities, e.g., in an amount of between 0.25 and 10% of the polymer weight, it was found that the subsequent product produced from this slurry exhibited both antimicrobial and antiviral properties.

Unlike the fibers described, e g. in WO 98/06508 and WO 98/06509, In which the fibers are coated on the outside, in the present product the polymer has microscopic water insoluble particles of ionic copper encapsulated therein with a portion of said particles being exposed and protruding from surfaces thereof. These exposed particles which protrude from the surface of the polymeric material have been shown to be active, as demonstrated by the tests set forth hereinafter.

In general, the products of the present invention are produced as follows:

1. A slurry is prepared from any polymer, the chief raw material preferably being selected from a polyamide, a polyethylene, a polyurethane and a polyester. Combinations of more than one of said materials can also be used provided they are compatible or adjusted for compatibility. The polymeric raw materials are usually in bead form and can be mono-component, bi-component or multi-component in nature. The beads are heated to melting at a temperature which preferably will range from about 120 to 180° C.

2. At the hot mixing stage, before extrusion, a water insoluble powder of ionic copper is added to the slurry and allowed to spread through the heated slurry. The particulate size will be preferably between 1 and 10 microns, however can be larger when the film or fiber thickness can accommodate larger particles.

3. The liquid slurry is then pushed with pressure through holes in a series of metal plates formed into a circle called a spinneret. As the slurry is pushed through the fine holes which are close together, they form single fibers or if allowed to contact one another, they form a film or sheath. The hot liquid fiber or film is pushed upward with cold air forming a continuous series of fibers or a circular sheet. The thickness of the fibers or sheet is controlled by the size of the holes and speed at which the slurry is pushed through the holes and upward by the cooling air flow.

4. In percentage mixtures of up to 10% by weight of ionic copper dust demonstrated, no degradation of physical properties in a polyamide slurry of the finished product. When tested, mixtures as low as 1% still showed antimicrobial properties, as well as surprisingly showing inhibition of HIV-1 activity.

In WO 94/15463 there are described antimicrobial compositions comprising an inorganic particle with a first coating providing antimicrobial properties and a second coating providing a protective function wherein said first coating can be silver or copper or compounds of silver, copper and zinc and preferred are compounds containing silver and copper (II) oxide. Said patent, however, is based on the complicated and expensive process involving the coating of the metallic compositions with a secondary protective coating selected from silica, silicates, borosilicates, aluminosilicates, alumina, aluminum phosphate, or mixtures thereof and in fact all the claims are directed to compositions having successive coatings including silica, hydrous alumina and dioctyl azelate.

In contradistinction, the present invention is directed to the use and preparation of a polymeric material, having microscopic water insoluble particles of ionic copper in powder form, which release $Cu^{++}$ encapsulated therein with a portion of said particles being exposed and protruding from surfaces thereof, which is neither taught nor suggested by said publication and which has the advantage that the exposed $Cu^{++}$ releasing water. Insoluble particles which protrude from the polymeric material have been proven to be effective even in the inhibition of HIV-1 activity.

In EP 427858 there is described an antibacterial composition characterized in that inorganic fine particles are coated with an antibacterial metal and/or antibacterial metal compound and said patent does not teach or suggest a polymer that incorporates microscopic water insoluble particles of ionic copper in powder form, which release $Cu^{++}$ encapsulated therein with a portion of said particles being exposed and protruding from surfaces thereof.

In DE 4403016 there is described a bacteriacidal and fungicidal composition utilizing copper as opposed to ionic $Cu^{++}$ and said patent also does not teach or suggest a polymer that incorporates microscopic water insoluble particles of ionic copper in powder form, which release $Cu^{++}$ encapsulated therein with a portion of said particles being exposed and protruding from-surfaces thereof.

In JP-01 046465 there is described a condom releasing sterilizing ions utilizing metals selected from copper, silver, mercury and their alloys which metals have a sterilizing and sperm killing effect, wherein the metal is preferably finely powdered copper. While copper salts such as copper chloride, copper sulfate and copper nitrate are also mentioned as is known these are water soluble salts which will dissolve and break down the polymer in which they are introduced. Similarly, while cuprous oxide is specifically mentioned this is a $C^+$ ionic form and therefore said patent does not teach or suggest the use of exposed $C^{++}$ releasing water insoluble particles which protrude from the polymeric material and which have been proven to be effective even in the inhibition of HIV-1 activity.

In JP01 246204 there is described an antimicrobial moulded article in which a mixture of a powdery copper compound and organic polysiloxane are dispersed into a thermoplastic moulded article for the preparation of cloth, socks, etc. Said patent specifically states and teaches that metal ions cannot be introduced by themselves into a polymer molecule and requires the inclusion of organopolysiloxane which is also intended to provide a connecting path for the release of copper ions to the fiber surface. Thus, as will be realized said copper compound will be encapsulated and said patent does not teach or suggest the use of exposed $C^{++}$ releasing water insoluble particles that protrude from the polymeric material.

In JP-03 113011 there is described a fiber having good antifungus and hygienic action preferably for producing underwear wherein said synthetic fiber contains copper or a copper compound in combination with germanium or a compound thereof, however, said patent teaches and requires the presence of a major portion of germanium and the copper compounds disclose therein are preferably metallic copper, cuprous iodide which is a monovalent $Cu^+$ compound and water soluble copper salts. Thus, said patent does not teach or suggest the use of exposed $Cu^{++}$ releasing water insoluble particles which protrude from the polymeric material.

In EP 116865 there is described and claimed a polymer article containing zeolite particles at least part of which retain at least one metal ion having a bacterial property and thus said patent does not teach or suggest the use of exposed $C^{++}$ releasing water insoluble particles, by themselves and in the absence of a zeolite, which particles protrude from the polymeric material and which have been proven to be effective even in the inhibition of HIV-1 activity.

In EP 253653 there is described and claimed a polymer containing amorphous aluminosilicate particles comprising an organic polymer and amorphous aluminosilicate solid particles or amorphous aluminosilicate solid particles treated with a coating agent, at least some of said amorphous aluminosilicate solid particles holding metal ions having a bactericidal actions. Thus, said patent does not teach or suggest the use of exposed $Cu^{++}$ releasing water insoluble particles, by themselves and in the absence of amorphous aluminosilicate particles, which exposed $C^{++}$ releasing water insoluble particles, protrude from the polymeric material and which have been proven to be effective even in the inhibition of HIV-1 activity.

Referring to the use of the material as a post harvest packaging system, it was found that microbes outside the package will not be able to enter the enclosed area and that microbes inside the packet will have difficulty in growing along the inside of the packaging material which is usually where they incubate due to condensation within the encapsulated area.

As indicated hereinabove, the polymeric material of the present invention, having microscopic particles of ironic copper encapsulated therein, can also be utilized to manufacture disposable gloves and condoms using a mold/form configuration.

In general, the chief raw material is concentrated and preserved natural rubber latex. In addition such chemicals as acid, chlorine gases, alkalis, and corn/maize starch can be added, as is known in the art, however according to the present invention there is also added CU++ in powder form.

Formers (or positive molds) are prepared through preparations that will keep the liquid latex from sticking thereto. This is done through a series of dips and treatments to the molds, as known per se in the art. The formers are then cleaned and dried and are dipped into a solution of coagulant chemicals. The coagulant forms a layer on the formers which helps to solidify latex when the formers are dipped into the latex tank.

The formers are dipped into the latex mixture, withdrawn therefrom and passed through a curing oven. The gloves and/or condoms will be vulcanized as they pass through the different areas of the oven which expose the same to temperatures ranging from about 120 to 140° C. This process cross-links the latex rubber to impart the physical qualities required.

The difference between the normal process of manufacturing a disposable glove/condom and the process of the present invention is the addition of the Cu++ powder in the raw materials.

While the invention will now be described in connection with certain preferred embodiments in the following examples and with reference to the attached figures, so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Figure 2:
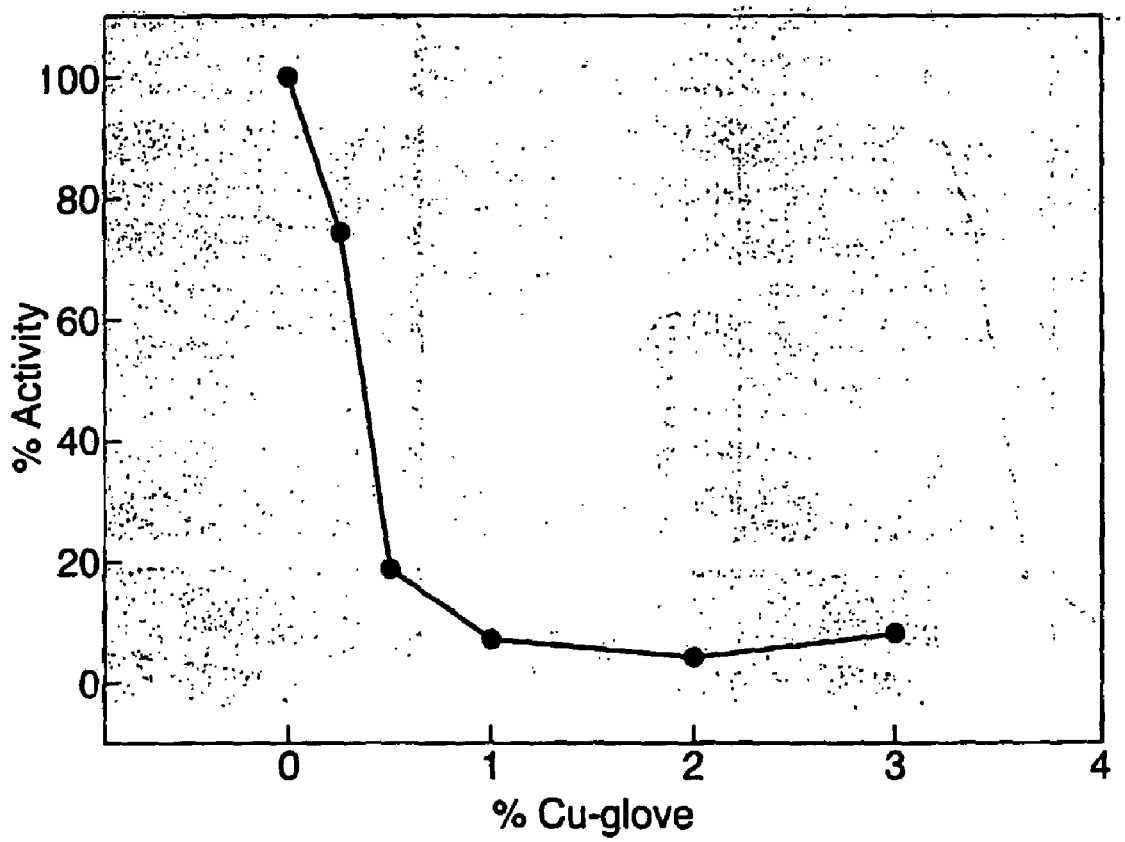

In the drawings:

FIG. 1 is an electron microscope photograph of a nylon fiber with copper particles embedded therein and protruding therefrom after having been added to a polymeric slurry; and FIG. 2 is a graphical representation of the inhibition of HIV-1 on sterilized pieces of latex gloves impregnated with varying amounts of ionic copper according to the present invention.

EXAMPLE 1

Preparation of Fibers

A total of 500 grams of a polyamide bi-component compound were prepared by heating the two beaded chemicals in separate baths each at 160° C.

The two separate components were then mixed together and allowed to stir for 15 minutes until the mixture appeared to be homogenous in color.

The mixed chemistry was again divided into two separate pots. In one pot, 25 grams of a mixture of $CuO$ and $Cu_2O$ powder was added yielding a 1% mixture. In the second pot 6.25 grams of a mixture of $CuO$ and $Cu_2O$ were added yielding a 0.25% mixture. In both cases, the temperature of 160° C. was maintained. The compounds were stirred until they appeared homogenous in color.

The two mixtures were run through a spinneret with holes that yielded fibers of between 50 and 70 microns in diameter. Since the Cu++ releasing powder was ground to particles of less than 20 microns no obstructions in the spinneret holes were observed. The extruded fibers were air-cooled and spun on to cones.

The fibers were tested for biological activity.

The difference between the normal process of manufacturing any synthetic fiber and this process is the addition of the Cu++ releasing powder in the raw materials.

EXAMPLE 2

100 µl aliquots of highly concentrated HIV-1 virus were incubated on top of the fibers for 30 minutes at 37° C. Then 10 µl of each pretreated virus were added to MT-2 cells (Lymphocyte Human Cell Line) cultured in 1 ml media. The cells were then incubated for 5 days in a moist incubator at 37° C. and the virus infectivity and proliferation was determined by measuring the amount of p24 (a specific HIV-1 protein) in the supernatant with a commercial ELISA (Enzyme Based Immuno-absorbtion Assay) kit. The results are the average of duplicate experiments. As control for possible cytotoxicity of the CuO or $Cu_2O$ to the cells, similar experiments were carried out as above, but the fibers were incubated with 100 µl of natural medium that did not contain HIV-1. No cytotoxicity was observed, i.e., none of the host cells were observed to be killed, under the experimental conditions described above.

The following summarizes the evaluation of the capacity of the several fibers impregnated with CuO and $Cu_2O$ to inhibit HIV-1 proliferation in tissue culture:

| | |
|---|---|
| Negative control (Polymeric Fiber without CuO and $Cu_2O$): | no inhibition |
| Positive control (CuO and $Cu_2O$ powder): | 70% inhibition |
| 1% CuO and $Cu_2O$ Fiber: | 26% inhibition. |

EXAMPLE 3

Antifungal Susceptibility Testing

Susceptibility testing was performed as follows:

Agar formulation used for this test was chosen in accordance with NCCLS document M27-A: RPMI (RPG) and a buffered to pH 7.0 with 0, 0.165 M morpholinepropane-sulfonic acid buffer (MOPS).

For the test, 90-mm-diameter plates containing agar at a depth of 4.0 mm were used. For *Candida albicans, Cryptococcus neoformans, micrococcus, Tinea pedis*, and *Tinea curpus*, the inoculum was prepared from a 24 hour culture and a 48 hour culture respectively; whereas for *Aspergillus fumigatus* and *Trichophyton mentagrophytes* a five-day old culture was used. Cell suspension was prepared in sterile 0.85% NaCl adjusted to a turbidity of a 0.5 McFarland standard. The agar surface was inoculated by streaking a nontoxic swab dipped in a cell suspension across the entire surface of the agar in three directions.

After excess moisture was absorbed into the agar and the surface was completely dry, Chemtex/MTC treated fibers+ in a concentration range from 3%–10% were applied to each plated. The plates were incubated at 35° C. and read after 24 hours, 48 hours, and 7 days. Antifungal activity of the treated fibers was considered positive if a zone of inhibition was visible underneath and surrounding the fibers.

Antibacterial Susceptibility Testing

Susceptibility testing was performed as described above for the antifungal activity with the following modifications: Mueller-Hinton agar (Difco, Detroit, Mich.) was the medium used. The pH was adjusted to 7.2–7.4. The bacteria used for this study were *Escherchia coli, Staphylococcus aureus, brevubactedum, acinetobacter* and *micrococcus*.

Results

The treated fibers in a concentration range of 3–10% exhibited characteristic inhibitory zone underneath and surrounding the fibers, indicating correct antifungal and antibacterial activity. The controls (untreated fibers) indicated no antifungal or antibacterial activity.

EXAMPLE 4

Fifty µl of RPMI 1640 medium, containing HIV-1 IIIB (laboratory T-tropic strain, 0.36 pg p24 [amount of virus]), were placed on top of UV sterilized pieces of gloves. As negative control for viral activity, 50 µl of medium was placed on the gloves, and as positive control, virus was placed on a regular glove (i.e. no Cu++). The experiment was done in duplicates, i.e., in each glove (different concentrations of Cu++) two separate drops with or without virus were placed.

After 20 minutes of incubation at room temperature, the 50 µl of drops containing the virus were mixed with 450 µl fresh medium (containing 10% fetal calf serum), and the mixture was added to $2 \times 10^5$ MT-2 cells (a lymphocyte cell line) in 1 ml medium (containing 10% fetal calf serum).

The virus-cell mixtures were then incubated in 24 well plates in a $CO_2$ humidified incubator at 37° C. After 4 days of incubation the amount of virus present per well was quantified by a Reverse Transcriptase (RT) Assay.

RT is a key enzyme of the HIV-1, which can polymerize a DNA strand from an RNA strand. By adding radio-labeled deoxynucleotides, the amount of newly synthesized DNA can be quantified. The percentage of inhibition as shown in FIG. 2 was calculated by dividing the average counts per minute (CPM) obtained in each glove concentration by that obtained in the regular control glove.

As will be noted from said graph, twenty minutes of exposure of concentrated HIV-1 virus to the surface of a latex glove impregnated with 1% or more of a copper ion yielding compound at room temperature resulted in a more than a 95% neutralization of subsequent virus infectivity of lymphocytes (the main target of HIV-1). This result points out the potential of an approach of impregnating copper into a slurry to form a glove or other item, such as a condom, to neutralize infectious viruses which may be found in human contaminated fluids such as blood or sperm. It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. An antimicrobial and antiviral polymeric material, comprising
   a polymer selected from the group consisting of polyamide, polyester, and polypropylene, and
   a single anti-microbial and anti-viral component consisting essentially of microscopic water insoluble particles of copper oxide incorporated in the polymer,
   wherein a portion of said particles in said polymer are exposed and protruding from the surface of the material,
   and wherein said particles release $Cu^{++}$ when exposed to water or water vapor.

2. An antimicrobial and antiviral polymeric material according to claim 1, wherein said polymeric material is a film.

3. An antimicrobial and antiviral polymeric material according to claim 1, wherein said polymeric material is a fiber.

4. An antimicrobial and antiviral polymeric material according to claim 1, wherein said polymeric material is a yarn.

5. An antimicrobial and antiviral polymeric material according to claim 1, wherein said particles are of a size of between 1 and 10 microns.

6. An antimicrobial and antiviral polymeric material according to claim 1, wherein said particles are present in an amount of between 0.25 and 10% of the polymer weight.

7. A wrapping material comprising an antimicrobial polymeric material according to claim 1.

8. An antimicrobial and antiviral polymeric material according to claim 1, wherein the particles are of a size of between 1 and 10 microns and are present in an amount of between 0.25 and 10% of the polymer weight.

9. An antimicrobial and antiviral polymeric material according to claim 1, wherein said polymer is polypropylene.

10. An antimicrobial and antiviral polymeric material according to claim 1, wherein said polymer is polyamide.

11. An antimicrobial and antiviral polymeric material according to claim 1, wherein said polymer is polyester.

12. A glove comprising the antimicrobial and antiviral polymeric material of claim 5.

13. A surgical tube comprising the antimicrobial and antiviral polymeric material of claim 5.

14. An antimicrobial and antiviral polymeric material according to claim 3, wherein the fiber is bi-component or multi-component.

15. The antimicrobial and antiviral polymeric material of claim 1, wherein said microscopic water insoluble particles of copper oxide consist of cupric oxide particles and cuprous oxide particles.

16. The antimicrobial and antiviral polymeric material according to claim 15, wherein said polymeric material is a film.

17. The antimicrobial and antiviral polymeric material according to claim 15, wherein said polymeric material is a fiber.

18. The antimicrobial and antiviral polymeric material according to claim 15, wherein said polymeric material is a yarn.

19. The antimicrobial and antiviral polymeric material according to claim 15, wherein said particles are of a size of between 1 and 10 microns.

20. The antimicrobial and antiviral polymeric material according to claim 15, wherein said particles are present in an amount of between 0.25 and 10% of the polymer weight.

21. A wrapping material comprising an antimicrobial polymeric material according to claim 15.

22. A condom comprising an antiviral polymeric material of claim 15.

23. An antimicrobial and antiviral polymeric material according to claim 15, wherein said particles are of a size of between 1 and 10 microns and are present in an amount of between 0.25 and 10% of the polymer weight.

24. A glove comprising the antimicrobial and antiviral polymeric material of claim 15.

25. A surgical tube comprising the antimicrobial and antiviral polymeric material of claim 15.

26. A glove comprising an antiviral polymeric material according to claim 1.

27. The glove of claim 26 wherein said microscopic water insoluble particles of copper oxide comprise cupric oxide particles and cuprous oxide particles.

28. Surgical tubing comprising an antiviral polymeric material according to claim 1.

29. The surgical tube of claim 28 wherein said microscopic water insoluble particles of copper oxide comprise cupric oxide particles and cuprous oxide particles.

30. A condom comprising an antiviral polymeric material, said material comprising
   a polymer selected from the group consisting of polyamide, polyester, and polypropylene, and a single anti-microbial and anti-viral component consisting essentially of microscopic water insoluble particles of copper oxide incorporated in the polymer,
   wherein a portion of said particles in said polymer are exposed and protruding from the surface of the material,
   and wherein said particles release $Cu^{++}$ when exposed to water or water vapor.

31. An antimicrobial and antiviral polymeric material, consisting essentially of a polymer selected from the group consisting of polyamide, polyester, and polypropylene, and a single anti-microbial and anti-viral component consisting essentially of microscopic water insoluble particles of copper oxide incorporated in the polymer, wherein a portion of said particles in said polymer are exposed and protruding from the surface of the material, and wherein said particles release $Cu^{++}$ when exposed to water or water vapor.

32. The polymeric material of claim 31, wherein said polymer is polypropylene.

33. The polymeric material of claim 31, wherein said polymer is polyamide.

34. The polymeric material of claim 31, wherein said polymer is polyester.

* * * * *

UNITED STATES PATENT AND TRADEMARK OFFICE
CERTIFICATE OF CORRECTION

PATENT NO.       : 7,169,402 B2                                    Page 1 of 1
APPLICATION NO.  : 10/240993
DATED            : January 30, 2007
INVENTOR(S)      : Jeffrey Gabbay It is certified that error appears in the above-identified patent and that said Letters Patent is hereby corrected as shown below:

Claim 1, column 9, line 2, please replace "Art" with --An--.

Signed and Sealed this

Fifteenth Day of May, 2007

JON W. DUDAS
*Director of the United States Patent and Trademark Office*